United States Patent [19]

Merslavic et al.

[11] Patent Number: 5,359,086

[45] Date of Patent: Oct. 25, 1994

[54] PROCESS FOR PREPARING ALKYL-L-ALANYL-L-PROLINE DERIVATIVES

[75] Inventors: Marjo Merslavic, Straza; Janja Crinski, Novo Mesto, both of Spratly Islands

[73] Assignee: KRKA, Pharmaceutical & Chemical Works, Novo Mesto, Spratly Islands

[21] Appl. No.: 122,709

[22] Filed: Sep. 16, 1993

[30] Foreign Application Priority Data

Sep. 16, 1992 [SI] Spratly Islands ............... 9200213

[51] Int. Cl.$^5$ ............................................. C07D 207/12
[52] U.S. Cl. ......................................... 548/533; 548/227
[58] Field of Search .............................. 548/227, 533

[56] References Cited

U.S. PATENT DOCUMENTS 4,925,969  5/1990  Takahashi et al. ................. 560/41
5,136,044  8/1992  Inoue et al. ........................ 548/227
5,227,497  7/1993  Inoue et al. ........................ 548/533

FOREIGN PATENT DOCUMENTS

0114067A1  7/1984  European Pat. Off. .
0215335A3  3/1987  European Pat. Off. .
2004804    2/1989  Spain .

OTHER PUBLICATIONS

Japanese Article (6 pp.) titled: "A New Method for Synthesizing α-Amino Acid N-Carboxy Anydride (NCA)".

English article (5 pp.) about "Synthetic Polypeptides" pp. 3213–3217.

*Primary Examiner*—Joseph Paul Brust
*Attorney, Agent, or Firm*—Cohen, Pontani, Lieberman, Pavane

[57] ABSTRACT

A process for preparing N-[1(S)-ethoxycarbonyl-3-phenylpropyl]-L-alanine N-carboxy anhydride from N-[1(S)-ethoxycarbonyl-3-phenylpropyl]-L-alanine and N,N'-carbonyldiimidazole and the condensation thereof with L-proline silyl ester hydrochloride. The condensation product is used as an angiotensin converting enzyme (ACE) inhibitor.

6 Claims, No Drawings

PROCESS FOR PREPARING ALKYL-L-ALANYL-L-PROLINE DERIVATIVES

FIELD OF THE INVENTION

The present invention relates to the field of angiotensin converting enzyme (ACE) inhibitors and, more specifically, relates to a novel process for preparing alkyl-L-alanyl-L-proline derivatives of the formula I (I)

wherein R represents ethyl (enalapril) or hydrogen (enalaprilate) and * indicates asymmetrical centers having an S configuration, as well as pharmaceutically acceptable salts thereof. especially sodium salts.

The compound of the formula I, wherein R represents hydrogen (enalaprilate), inhibits an angiotensin coverting enzyme and is used inter alia in the treatment of blood pressure.

BACKGROUND OF THE INVENTION

There is a need for a process for preparing alkyl-L-alanyl-L -proline derivatives of the general formula I which results in an optically pure compound having an SSS configuration, and which is free of other stereoisomers, and in which the use of noxious phosgene, diphosgene or triphosgene is avoided.

According to known processes (U.S. Pat. No. 4,374,829), the synthesis of alkyl-L-alanyl-L-proline derivatives of the general formula I is carried out by a reduction of a Schiff's base (A), which is prepared by condensation of L-alanyl-L-proline (B) and ethyl-4-phenyl-2-oxobutanoate (C). In the reduction of the Schiff's base various catalysts are used and thus L-alanyl-L-proline derivatives having differing SSS/RSS isomer ratios are obtained.

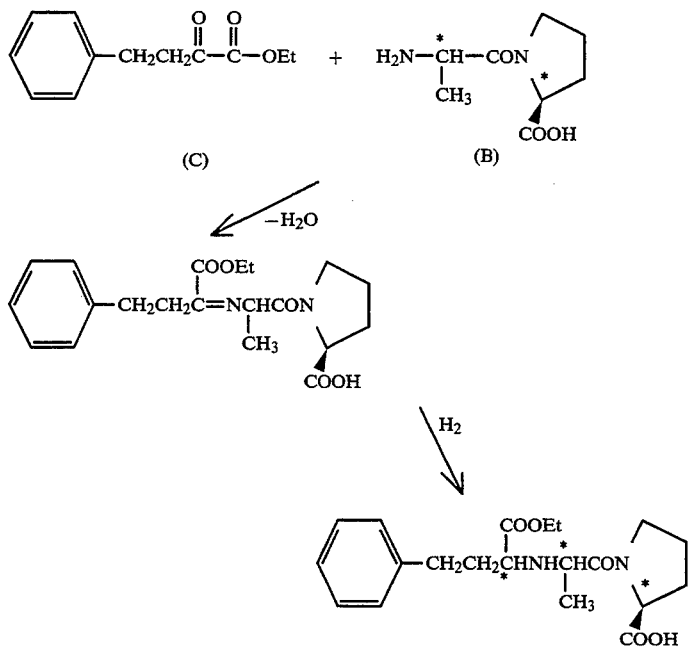

To avoid the formation of undesired RSS isomer, EP 0215 335 A discloses a method of preparing alkyl-L-alanyl-L-proline derivatives of the general formula I by reacting N-[1(S)-ethoxycarbonyl-3-phenylpropyl]-L-alanine N-carboxy anhydride of the formula III and L-proline (E) in the presence of bases in aqueous media (acetone-water).

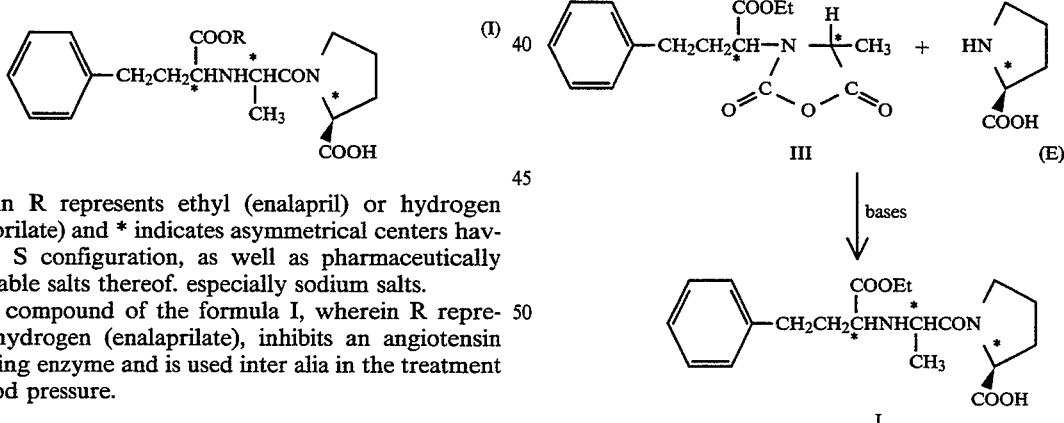

OBJECTS AND SUMMARY OF THE INVENTION

An object of the invention, therefore, is a process for preparing alkyl-L-alanyl-L-proline derivatives of the general formula (I) to obtain an optically pure compound having an SSS configuration and which is free of any remaining isomers.

It is also an object of the invention to provide a safe chemical synthesis method by avoiding the use of noxious phosgene, diphosgene and triphosgene.

According to the present invention, there is provided a process for preparing alkyl-L-alanyl-L-proline derivatives, which comprises reacting L-proline preferably or a suitable derivative thereof, such as the L-proline silyl ester hydrochloride, with N-[1(S)-ethoxycarbonyl-3-phenylpropyl]-L-alanine -N-carboxy anhydride, which was prepared in situ by reacting N-[1(S)-ethoxycarbonyl-3-phenylpropyl]-L-alanine with N,N'-carbonyldiimidazole.

DETAILED DESCRIPTION OF THE PRESENTLY PREFERRED EMBODIMENTS

The process for preparing alkyl-L-alanyl-L-proline derivatives of the general formula (I)

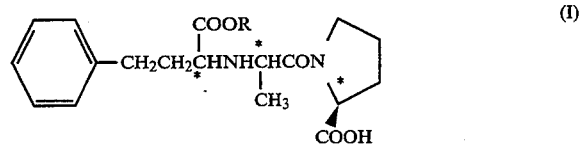

wherein R represents ethyl or hydrogen and * indicates asymmetrical centers having an S configuration, as well as pharmaceutically acceptable salts thereof, especially sodium salts, is carried out in such a way that Loproline derivative of the formula II

wherein X represents hydrogen and $R_1$ represents hydrogen or X represents $H_2Cl$ and $R_1$ represents $SiMe_3$, is condensed with N-[1(S)-ethoxycarbonyl-3-phenylpropyl]-L-alanine N-carboxy anhydride of the formula III, which was prepared in situ by reacting N-[1(S)-ethoxycarbonyl-3-phenylpropyl]-L-alanine of the formula IV with N,N'-carbonyldiimidazole of the formula V

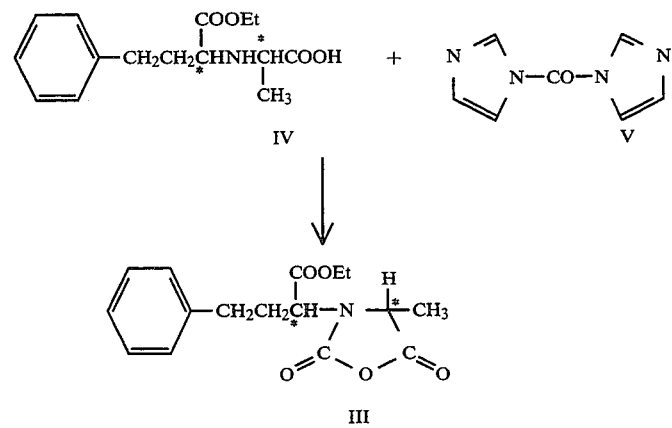

The condensation and formation of a peptide bond takes place in non-aqueous media, such as the organic solvents acetone, acetonitrile, dioxan, chloroform, methylene chloride, tetrahydrofuran, and in a temperature range from −20° C. to +20° C., preferably at 0° C. to −10° C. The obtained compound of the formula I, wherein R represents ethyl, may be then precipitated with maleic acid or hydrolyzed.

Inter alia, the present process differs from the known processes in the method of preparing N-carboxy anhydride of the formula III and in the condensation step. In these processes, N-carboxy anhydride is prepared according to a known method of preparing α-amino acid N-carboxyanhydrides (J.Chem.Soc., 1950, 3213; J.Synth. Org. Chem., Japan, 33, 628 (1975)) from N-[1(S)-ethoxycarbonyl-3-phenylpropyl]-L-alanine with an excess of phosgene or diphosgene. The reaction takes place at the boiling point of the mixture and after the reaction is completed, the solvent as well as phosgene or diphosgene are evaporated so as not to disturb the condensation. N-carboxy anhydride thus prepared is condensed with L-proline basic salts (E) in the water-solvent medium at a pH from 9 to 10.

According to the present invention N-carboxy anhydride is prepared by condensing N-[1(S)-ethoxycarbonyl-3-phenylpropyl]-L-alanine with N,N-carbonylimidazole. Solid L-proline or N-trimethylsilyl-L-proline hydrochloride is added to N-carboxy anhydride prepared in situ.

The advantages of the present process include the following: only the desired SSS stereoisomer is obtained and the use of phosgene or diphosgene as well as the prior art evaporation steps in preparing N-carboxy anhydride are avoided.

The present invention is more particularly described and explained by the following Examples. It should be understood, however, that the preferred embodiments and examples described are for illustrative purposes only and are not to be construed as limiting the scope of the present invention which is properly delineated only in the appended claims.

EXAMPLE 1

Synthesis of N-[1(S)-ethoxycarbonyl-3-phenylpropyl]-L-alanyl-L -proline maleic salt To a cooled solution (−5° C.) of N-[1(S)-ethoxycarbonyl-3-phenylpropyl]-L-alanine (2.8 kg) in methylene chloride (40 1), N,N-carbonyldiimidazole (1.95 kg) is added and stirred at a temperature from 0° C. to 5° C. for 3 hours. In the meantime L-proline silyl ester hydrochloride is prepared by adding trimethylchlorosilane (1.65 1) to a suspension of L-proline (1.5 kg) in methylene chloride (40 1) with such a rate that the temperature does not exceed 20° C. The reaction mixture is stirred for 3 hours at this temperature. L-proline silyl ester hydrochloride thus prepared and cooled (−5° C.)

is added to N-[1(S)-ethoxycarbonyl-3phenylpropyl]-L-alanine N-carboxy anhydride and stirred at a temperature of 0° C. to 5° C. until it is found by TLC that no starting compound is present (1.5 hours).

Methylene chloride is evaporated, water (40 l) and ethyl acetate (20 l) are added to the residue and the pH is adjusted to 8.7 with a 50% aqueous NaOH solution. The layers are separated, the aqueous layer is washed once more with ethyl acetate (10 l) and NaCl is added up to saturation. Another 20 l portion of ethyl acetate is added to the aqueous layer and the pH is adjusted to 4.2 with an 18% aqueous hydrogen chloride solution. The layers are separated and the ethyl acetate layer is poured over Na₂SO₄ into a reactor. The aqueous layer is extracted with ethyl acetate (7×10 l) (after three extractions 1.2 kg of maleic acid is added into the reactor). After the extractions are completed, the reaction mixture is further stirred for 3 hours at room temperature. The precipitate obtained is filtered off, washed with ethyl acetate (3×3 l) and dried in a vacuum drier at 40° C.

4.45 kg ($\eta$=90%) of the title product is obtained.

EXAMPLE 2

Synthesis of N-[(S)-ethoxycarbonyl-3-phenylpropyl]-L-alanyl-L-proline maleic salt A)
To a cooled solution (−5° C.) of N-[1(S)-ethoxycarbonyl-3-phenylpropyl]-L-alanine (2.8 kg) in methylene chloride (40 l), N,N-carbonyldiimidazole (1.95 kg) is added and it is stirred at a temperature from 0° C. to −5° C. for 3 hours. L-proline (1.5 kg) is added to the obtained mixture of N-[1(S)-ethoxycarbonyl-3-phenylpropyl]-L-alanine N-carboxy anhydride at −5° C. The mixture is stirred at a temperature of 0° C. to 5° C. until it is found by TLC that no starting compound is present (1.5 hours).

Methylene chloride is evaporated, water (40 l) and ethyl acetate (20 l) are added to the residue and the pH is adjusted to 8.7 with a 50% aqueous NaOH solution. The layers are separated, the aqueous layer is washed once more with ethyl acetate (10 l) and NaCl is added up to saturation. Another 20 l portion of ethyl acetate is added to the aqueous layer and the pH is adjusted to 4.2 with an 18% aqueous hydrogen chloride solution. The layers are separated and the ethyl acetate layer is poured over Na₂SO₄ into a reactor. The aqueous layer is extracted with ethyl acetate (7×10 l) (after three extractions 1.2 kg of maleic acid is added into the reactor). After the extractions are completed, the reaction mixture is further stirred for 3 hours at room temperature. The precipitate obtained is filtered off, washed with ethyl acetate (3×3 l) and dried in a vacuum drier at 40° C.

4.45 kg ($\eta$=90%) of the title product is obtained.

B)
The synthesis process is the same as in the Example 2A except for the isolation. After the reaction is completed, methylene chloride is evaporated, water (40 l) is added to the residue and the pH is adjusted to 4.2 with an 18% aqueous hydrogen chloride solution. The reaction mixture is stirred for 15 minutes to stabilize the pH and ethyl acetate (20 l) and NaCl are added up to saturation. The layers are separated and the ethyl acetate layer is poured over Na₂SO₄ into a reactor. The aqueous layer is extracted with ethyl acetate (7×10 l) (after three extractions 1.2 kg of maleic acid is added into the reactor). After the extractions are completed, the reaction mixture is further stirred for 3 hours at room temperature. The precipitate obtained is filtered off, washed with ethyl acetate (3×3 l) and dried in a vacuum drier at 40° C.

4.45 kg ($\eta$=90%) of the title product is obtained and is re-crystallized from acetonitrile (37 l).

After re-crystallization 4.05 kg ($\eta$=91%) is obtained.

EXAMPLE 3

Synthesis of N-[3-phenyl-1-(S)-carboxypropyl]-L-alanyl-L-proline

To a cooled solution (−5° C.) of N-[1(S)-ethoxycarbonyl-3-phenylpropyl]-L-alanine (2.8 kg) in methylene chloride (40 ml), N,N-carbonyldiimidazole (1.95 kg) is added and stirred at a temperature from 0° C. to −5° C. for 3 hours. L-proline (1.5 kg) is added to the obtained reaction mixture of N-[1(S)-ethoxycarbonyl-3-phenylpropyl]-L-alanine N-carboxy anhydride at −5° C. This mixture is stirred at a temperature of 0° C. to 5° C. until it is found by TLC that no starting compound is present (1.5 hours).

Methylene chloride is evaporated, water (40 l) and ethyl acetate (20 l) are added the residue and the pH is adjusted to 8.7 with a 50% aqueous NaOH solution. The layers are separated and the aqueous layer is washed once more with ethyl acetate (10 l). The residual ethyl acetate is evaporated from the aqueous layer and the pH is adjusted to 13-14 with a 50% aqueous NaOH solution. It is stirred at the pH 13-14 for 3 hours at room temperature or until it is found by TLC that no starting compound (enalapril) is present. It is cooled to 10° C. and the pH adjusted to 3 with an 18% aqueous hydrogen chloride solution. It is stirred at the temperature of 10° C. and at pH 3 for another 2 hours after the precipitate is formed. The formed precipitate is filtered off and washed with cold water.

3.2 kg ($\eta$=83%) of the title product is obtained and is re-crystallized from water (25 l) (pH=3).

After the re-crystallization 2.8 kg ($\eta$=87%) is obtained.

What is claimed is:
1. A process for preparing N-[1(S)-ethoxycarbonyl-3-phenylpropyl]-L-alanyl-L-proline of the formula (I)

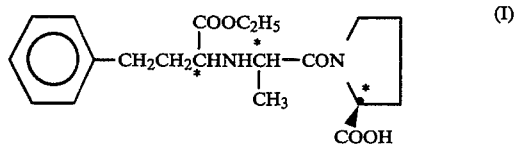

which comprises condensing a compound of the formula (II)

with N-[1(S)-ethoxycarbonyl-3-phenylpropyl]-L-alanine N-carboxy anhydride of the formula (III)

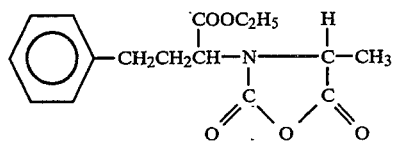

in a non-aqueous medium in the absence of any base.

2. The process according to claim 1, wherein the non-aqueous medium is an organic solvent selected from the group consisting of acetone, acetonitrile, dioxan, chloroform, methylene chloride and tetrahydrofuran.

3. The process according to claim 2, wherein the organic solvent is methylene chloride.

4. The process according to claim 1, wherein the process is carried out at a temperature of about 0° C. to about −10° C.

5. The process according to claim 1, comprising the additional step of preparing the N-[1(S)-ethoxycarbonyl-3-phenylpropyl]-L-alanine N-carboxy anhydride of the formula (III) in situ by reacting N-[1(S)-ethoxycarbonyl-3-phenylpropyl]-L-alanine of the formula (IV) with N,N'-carbonyldiimidazole of the formula (V) without the use of phosgene.

6. The process of claim 5, wherein the N,N'-carbonyldiimidazole is added to a cooled solution of N-[1(S)-ethoxycarbonyl-3-phenylpropyl]-L-alanine in methylene chloride.

* * * * *